(12) United States Patent
Sidebotham

(10) Patent No.: US 8,778,030 B2
(45) Date of Patent: Jul. 15, 2014

(54) LOAD BEARING IMPLANTS

(76) Inventor: Christopher G. Sidebotham, Mendham, NJ (US)

( * ) Notice: Subject to any disclaimer, the term of this patent is extended or adjusted under 35 U.S.C. 154(b) by 163 days.

(21) Appl. No.: 13/065,597

(22) Filed: Mar. 24, 2011

(65) Prior Publication Data

US 2012/0245700 A1 Sep. 27, 2012

(51) Int. Cl.
*A61F 2/36* (2006.01)
*A61F 2/30* (2006.01)

(52) U.S. Cl.
CPC ............. *A61F 2/3662* (2013.01); *A61F 2/3676* (2013.01); *A61F 2002/3692* (2013.01); *A61F 2002/30566* (2013.01)
USPC ................... 623/23.32; 623/23.17; 623/23.33

(58) Field of Classification Search
CPC ................ A61F 2/3662; A61F 2/3676; A61F 2002/3692; A61F 2002/30566
USPC .................................. 623/23.17, 23.31–23.33
See application file for complete search history.

(56) References Cited

U.S. PATENT DOCUMENTS

| | | | |
|---|---|---|---|
| 4,314,381 A | 2/1982 | Koeneman | 623/23.17 |
| 4,743,263 A | 5/1988 | Petrtyl et al. | 623/23.18 |
| 4,851,008 A | 7/1989 | Johnson | 623/23.5 |
| 4,938,774 A * | 7/1990 | Tepic | 623/23.32 |
| 5,041,118 A * | 8/1991 | Wasilewski | 606/85 |
| 5,549,702 A | 8/1996 | Ries et al. | 623/23.32 |
| 6,093,209 A | 7/2000 | Sanders | 623/23.33 |
| 6,245,112 B1 | 6/2001 | Doubler et al. | 623/22.41 |
| 6,652,591 B2 * | 11/2003 | Serbousek et al. | 623/23.31 |
| 6,723,129 B2 | 4/2004 | Dwyer et al. | 623/22.42 |
| 2002/0111692 A1 | 8/2002 | Ralph et al. | 623/23.17 |
| 2004/0107001 A1 | 6/2004 | Cheal et al. | 623/22.42 |
| 2007/0116734 A1* | 5/2007 | Akash | 424/423 |
| 2007/0233095 A1 | 10/2007 | Schlaepfer | 606/279 |
| 2008/0161931 A1 | 7/2008 | Perez-Cruet et al. | 623/17.16 |

* cited by examiner

*Primary Examiner* — David H Willse
*Assistant Examiner* — Javier Blanco
(74) *Attorney, Agent, or Firm* — Ernest D. Buff & Associates, LLC; Margaret A. LaCroix; Ernest D. Buff

(57) ABSTRACT

A load bearing implant comprising a femoral implant stem made from a bio-compatible metal having an elastic modulus far greater than that of natural bone. When the implant heals within a bone cavity, the implant essentially carries substantially the entire load. Transfer of load to the surrounding bone tissue is lost due to lack of use after healing. Flexing a stiff implant applies a large load at the implant distal end. The bone cortex is thereby allowed to thicken, causing thigh pain long after implant healing. The femoral implant has a bone ingrowth coating on the proximal end, allowing firm attachment of the implant in the bone cavity. The distal end has a central aperture and a helical machined groove that permits flexing of the distal portion of the femoral implant stem. This flexing occurs in a manner similar to surrounding bone tissue, preventing thigh pain.

8 Claims, 5 Drawing Sheets

Different Surfaces for Bone Growth Attachment

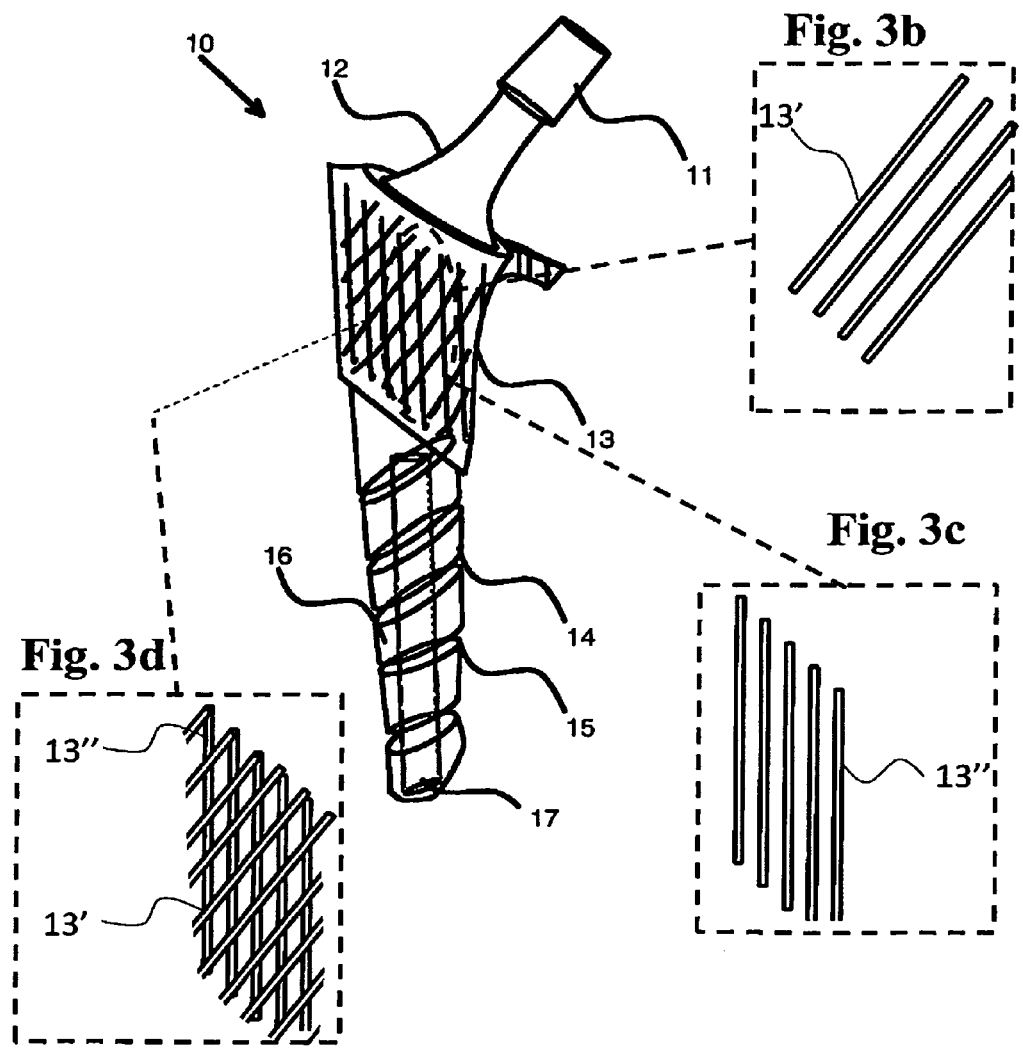

Hip Stem

Knee Femoral
Component

Knee Tibial
Component

Shoulder Humeral
Component

Elbow Humeral
Component

Hip Conservative
Femoral Component

Trauma
Bone Plate

Trauma
Locking Nail

LOAD BEARING IMPLANTS

BACKGROUND OF THE INVENTION

1. Field of the Invention

The present invention relates to implants; and more particularly to an implant that has flexural characteristics and load bearing qualities similar to a natural bone thereby preventing bone loss surrounding the implant due to lack of bone load bearing requirements.

2. Description of the Prior Art

Implants are generally made from bio-compatible materials such as titanium alloys or cobalt chromium alloys. These metallic implants have very high elastic modulus as compared to bone tissue. As a result, any load that is applied is almost entirely carried by the high elastic modulus material sparing the bone of its load bearing function. This results in bone thinning after the implant has healed. A number of prior art patents disclose attempts to solve this problem.

U.S. Pat. No. 4,743,263 to Petrtyl et al. discloses an adaptable isoelastic hip-endoprosthesis. The adaptable isoelastic hip endoprosthesis comprises a joint piece connected to a shaft of the endoprosthesis that is to be implanted in the femur. The shaft is composed of at least two spirally twisted elastic rods. The elastic rods at their lower end are mutually connected to act as stabilization bodies. The adaptable isoelastic hip-endoprosthesis disclosed by the '263 patent is a twisted spiral rod construction which applies force to the prepared bone cavity providing implant stability. When the scar is healed, the spring-like implant is said to form a unitary elastic object. However, the elastic modulus of the rods is very dissimilar to that of bone and the bone may not fuse to the implant due to the absence of a porous bone ingrowth surface. Application of any compressive force to the implant results in further expansion of the twisted rods resulting in permanent enlargement of the bone cavity, which will dislodge the implant.

U.S. Pat. No. 4,851,008 to Johnson discloses a bone implant prosthesis with a substantially stress-free outer surface. This bone implant prosthesis has an outer stress-free surface and a subsurface carried generally beneath and parallel to the outer surface, for bearing tensile stresses. The prosthesis includes a plurality of slots undercutting the outer surface of the prosthesis thus forming a stress bearing subsurface that frees the outer surface from substantial tensile stresses. The stress-free outer surface is readily adaptable to receive a porous coating that enhances bone ingrowth without decreasing the stress resistance characteristics of the prosthesis. The sub-surface is substantially smooth and free of stress concentration sites. The cross bar portions connecting T-shaped slots defines a stress-bearing, discontinuous, smooth subsurface generally parallel to and spaced beneath the outer surface of the prosthesis. The bone implant prosthesis disclosed by the '008 patent utilizes a row of T shaped slots formed by passing an electrode through the bone implant prosthesis melting a straight line path layer over the outer surface with T slots, a high modulus surface. When the implant is flexed, the distal portion of the implant still carries all of the flexural load and therefore does not prevent bone thinning. The portions of the implant through which the electrodes are not passed provides highly stressed areas and the T shaped portions only occupy a minority portion of the overall implant surface.

U.S. Pat. No. 5,549,702 to Ries et al. discloses a flexible orthopaedic stem apparatus. This orthopaedic prosthesis for implantation in a patient's intramedullary canal includes a rigid proximal portion sized and shaped to fit the intramedullary canal of a patient's bone and a lower elongated stem member with an outer surface and distal end. The lower stem member has a helical groove of varying width and depth on the outer surface and a hollowed tapered central core cooperating to enable flexing of the distal end. The flexible orthopaedic stem apparatus of the '072 disclosure has an implant with its distal portion having a helical groove on its surface of varying width and depth while the interior of the stem has a conical core that increases in diameter as it progresses towards the distal tip. This means that the thickness of the distal end decreases to very small value near the distal tip and may permanently deform the implant within the bone after insertion failing to provide adequate support during implant healing. Besides, the permanently deformed tip of the implant may create enormous pain to the patient. The rigid proximal portion of the implant is not indicated to have a porous bone ingrowth coating.

U.S. Pat. No. 6,093,209 to Sanders discloses a proximally hollow prosthesis. The proximally hollow prosthesis has a cap element and a stem. The prosthesis cap element is adapted to a ball and a stem suitable to be implanted in a reamed femoral medullary canal. The stem of the prosthesis has a proximal region and a distal region and is mateable with the cap element of the prosthesis. The proximal region has a circumferential wall defining a hollow cavity terminating to an open proximal end. The hollow cavity has a predetermined length keeping the cavity entirely within proximal region of the stem sufficient to allow the stem to flex, The distal region of the stem is located distal to the isthmus region of the stem and is made of solid metal or alloys. Any flexure of this implant strictly relies on the small wall thickness at the proximal cavity, but the large diameter at the proximal portion has a high moment of inertia providing very little flexing action since the metal or alloy used has a high elastic modulus.

U.S. Pat. No. 6,245,112 to Doubler et al. discloses a joint prosthesis having variable flexibility. The joint prosthesis has a coil spring at its lower end supported by a control rod, which applies compression to the coil spring. Since the central rod supports all the flexibility of the spring, the flexibility of the entire implant is only dependent on the flexibility of the control rod. Since the control rod is held in place securing the spring, any movement in these attachment means will result in unsupported non recoverable movement of the spring.

U.S. Pat. No. 6,723,129 to Dwyer et al. discloses a self-locking modular prosthesis having taper feature and associated method. The modular femoral prosthesis includes a stem member adapted to be implanted into a medullary canal of a femur. The stem member has a continuously tapered elongated bore and a threaded aperture defined therein. A first end of the elongated bore defines a post-receiving opening. The post-receiving opening is defined in a proximal end surface of the stem member. The elongated bore extends between the post-receiving opening and a threaded aperture. The femoral prosthesis also includes a neck member having a neck body, and a head-receiving support member secured to the neck body so as to extend outwardly there from. A tapered post is also secured to the neck body so as to extend outwardly there from. The tapered post is adapted to be received into the elongated bore of the stem member. The tapered post of the stem member has a proximal end and a distal end, and the tapered post is continuously tapered from said proximal end thereof to said distal end. The distal stem component may be provided in a number of different configurations in order to fit the needs of a given patient's anatomy and provide a variety of fixation options (e.g. textures and geometries) and sizes. Moreover, the distal stem component may also be provided in a bow-shaped configuration if required by a given patient's anatomy. This modular implant is not flexible, but is permanently bent according to the femoral cavity shape of the patient.

U.S. Patent Application Publication No. 2002/0111692 to Ralph et al. discloses an artificial hip having a femoral stem portion, which provides for micromovement. The femoral stem member is for use in an artificial hip implant assembly and comprises a shaft portion having a proximal end and a distal end. The distal end is shaped for insertion into the axial bore of a patient's femur. The proximal end includes a ball-shaped surface for insertion into a receiving cup disposed in an acetabular recess in said patient's pelvis. A helical cut is formed in the proximal shaft portion or distal shaft portion such that the helically cut segment of the shaft portion has an elastic modulus. The elastic modulus is substantially less than that of the remaining portions of the stem and approximates that of the patient's bone. The helical cuts form a restoring force spring-like shock absorbing geometry, which permits the rigid metal material to grossly conform to the elastic modulus of the patient's bone. The helical cut is formed in a segment of the proximal end or distal end of the shaft portion and has a polymer sheath that prevents the patient's bone ingrowth into the helical cuts, thus preventing interference with the geometric modification of the overall modulus of elasticity of the helically cut segment. The polymer sheath prevents bone ingrowth and attachment of the implant to the bone. The shaft is solid and does not have a central constant diameter aperture facilitating the bending of the shaft at the distal end.

U.S. Patent Application Publication No. 2004/0107001 to Cheal et al discloses a joint prostheses and components thereof. The joint prostheses of the '001 patent application provides a modular femoral stem that may be rotated after insertion and its neck length adjusted. The fluting or ridge formation in the mid section of the stem is indicated to allow rotation of the implant during insertion and may provide increased flexibility. It is not clear how a longitudinal flute or slot provides any flexibility to any portion of the stem. The '001 patent disclosure does not provide a stem with a proximal potion having bone ingrowth coating and a distal end having a central cylindrical aperture and a helical slot cut in the outer surface to allow flexing of the stem at its distal end.

U.S. Patent Application Publication No. 2007/0233095 to Schlaepfer discloses a device for dynamic stabilization of bones or bone fragments. The device for dynamic stabilization of bones or bone fragments comprises an anchor member for attachment to vertebrae having an opening configured to receive a longitudinal member and the longitudinal member being viscoelastically deformable and having a predetermined bending resilience. This stabilization structure stabilizes the spinal column of a patient.

U.S. Patent Application Publication No. 2008/0161931 to Perez-Cruet et al. discloses a vertebral disc annular fibrosis tensioning and lengthening device. The vertebral disc annular fibrosis tensioning and lengthening device restores the loss of disc height as a result of disc degeneration and other factors. The vertebral disc annular fibrosis tensioning and lengthening device includes pedicle screws having heads with cup-shaped cavities. The pedicle screws are threaded into the vertebral bodies of adjacent vertebrae through the pedicles so that open parts of the heads of the pedicle screws face each other. A spring is inserted into the cup-shaped cavities in compression so that the spring bias forces the pedicle screws apart, thus increasing the height of the disc space. The disclosed device is not a femoral stem.

Foreign Patent Application No. GB2078523, also U.S. Pat. No. 4,314,381 to Koeneman discloses a hip joint prosthesis. The hip joint prosthesis in which the stem portion of the femoral head prosthesis includes at least one layer of elastomeric material disposed between and attaching to at least two sections of rigid material to reduce necrosis and resorption of the adjacent bone. The hip joint prosthesis of the '523 patent application is a stem with two or four metal stem pieces with an elastomer sandwiched between them. This arrangement is indicated to prevent bone resorption due to the reduction of the stiffness of the implanted stem. Specifically, the stem of the '523 patent application does not have a helical slot formed on the outer surface of the distal portion of the stem providing flexibility only at the distal end. Also, the stem of the '523 application is solid and does not have a central cylindrical aperture.

There remains a need in the art for implants of different geometry made from bio-compatible high elastic modulus alloys that can be inserted into bone cavity that does not result in patient pain after the implant has healed and does not result in bone tissue loss due to excess load bearing capacity of the high modulus sparing the bone tissue from its load carrying functionality.

SUMMARY OF THE INVENTION

The present invention provides improved load bearing implants comprising a taper fitting with a locking taper, a neck-collar area to provide an anatomical distance compatible with soft tissue, a proximal body and distal body, The proximal body having a macro porous surface for bone ingrowth preferably comprising longitudinal cuts for stress reduction, and a hollow distal stem that has flexural cuts along the shaft, having a hollow centerline. The flexural cuts are a distance apart to prevent adjacent surfaces from touching. The flexural cuts comprise a combination of spiral, longitudinal and/or horizontal cuts. The flexural cuts are machined and may be in the form of helical cuts, longitudinal or horizontal cuts.

The present invention involves improved load bearing implants, as described below. Particularly, the load bearing implants generally comprise: (i) a taper fitting having a locking taper which provides for a head to attach, wherein said head has an internal female taper that locks onto a femoral implant stem; (ii) a neck-collar area providing an anatomical distance between a center of said head and a position of said implant during implantation so as to provide appropriate stretch for soft tissue; (iii) a femoral stem comprising a proximal portion generally having a macro porous surface adapted for bone ingrowth; (iv) said proximal portion having longitudinal cuts to reduce the stress level at the implant proximal location and transferring stress to the proximal bone body thereby preventing long term bone resorption; (v) a femoral stem having a tapered distal portion that has a cylindrical constant diameter hole or aperture with a wall thickness decreasing towards the distal end; (vi) said distal stem having lateral flexural cuts preferably in the form of a helix forming segments along its length providing flexure to said distal portion of the stem. The tapered distal portion of the stem includes an aperture along a centerline allowing the distal end and the lateral cuts to provide elastic flexure with a modulus of elasticity similar to the surrounding bone, and wherein said lateral flexural cuts are of a sufficient width and depth and spacing to prevent adjacent surfaces of said segments from touching. Preferably the flexural cuts form a spiral configuration yielding spiral segments along its length that provide flex to the hollow distal stem. Additionally, the lateral flexural cuts may be combined with longitudinal cuts relative to the implant centerline, or inclined cuts relative to the implant centerline, and/or a combination of spiral, longitudinal and/or inclined cuts.

The improved load bearing implant, comprises:

a. a femoral implant stem having a male locking tapered fitting adapted for attachment to a internal female taper of a head that locks the head to a femoral implant stem;

b. a neck-collar area providing an anatomical distance between a center of said head and a position of said femoral implant stem during implantation so as to provide appropriate stretch for soft tissue;

c. said femoral implant stem being made from biocompatible metal having a proximal portion and a tapered distal portion;

d. said proximal portion of femoral implant stem being solid and coated with a bone ingrowth coating having an attachment feature for firm attachment to bone within a bone cavity;

e. said proximal portion having a plurality of modulus decreasing features including longitudinal, inclined stress reducing cuts or slots thereby increasing load transfer to the bone area in the proximal region and preventing long term bone resorption;

f. said tapered distal portion having a cylindrical, constant diameter, central aperture whereby the wall thickness in the distal portion decreases progressively towards the distal end;

g. said tapered distal portion having a plurality of modulus decreasing features including lateral cuts or slots on the outer surface, preferably forming a continuous helix;

h. said cuts or slots having a pre-selected uniform width and a uniform depth and being spaced apart at a distance from each other so that the slots, in combination with the central taper, allow flexing of the distal portion;

whereby the combination of cuts or slots in the distal portion and central cylindrical aperture allow progressive flexing of the distal end, thereby minimizing excessive loading of the bone tissue, and appropriate selection of slots, depth of slots and spacing between slots prevents metal to metal contact on the adjacent surfaces of the cuts or slots during flexure, preventing generation of wear debris.

The bone implant may be of other configurations taking advantage of the improved elastic modulus compliance with the bone tissue. The implant configurations include hip stem for a total hip replacement, femoral head replacement for the hip, knee femoral component, knee tibial component, humeral component for a shoulder replacement, elbow replacement humeral component, bone plates and interlocking nails.

BRIEF DESCRIPTION OF DRAWINGS

The invention will be more fully understood and further advantages will become apparent when reference is had to the following detailed description of the preferred embodiments and the accompanying drawings, in which:

FIG. 3a illustrates the improved load bearing implant;

FIG. 3b illustrates a cross-sectional view of FIG. 3a showing a blow-up of inclined cuts relative to the implant centerline in the proximal portion;

FIG. 3c illustrates a cross-sectional view of FIG. 3a showing a blow-up of longitudinal cuts relative to the implant centerline in the proximal portion;

FIG. 3d illustrates a cross-sectional view of FIG. 3a showing a blow-up of longitudinal and inclined cuts relative to the implant centerline in the proximal portion;

DESCRIPTION OF THE PREFERRED EMBODIMENTS

There are many implants designed to replace the articular surface of the human joints. These implants include hip, knee, elbow, shoulder and ankle replacements. The implant designs address two basic principles: (i) replacing the bearing surface of the joint for motion; and (ii) providing a method of fixing the implant to the body. The former design feature has evolved over the past fifty years to include various metals, plastics, ceramics and coatings, which provide low-friction movement with minimal generation of wear debris. These bearing surfaces include a cobalt chrome alloy against ultra high molecular weight polyethylene (UHMWPE), titanium nitride coated metals against UHMWPE, ceramic against ceramic, metal against metal and combinations of these. The results for these bearing surfaces continue to improve the longevity of these implant replacements. Wear debris has been shown to cause bone resorption leading to loosening of the implant from the bone. The latter design feature of fixing the implant to the bone has been accomplished by two primary methods: (a) Bone cement (PMMA); (b) Bone ingrowth through porous surfaces (biologic fixation).

There exists a need in the art for a biologic fixation of prostheses that eliminates the necessity for cement; this need has been recognized in many clinical cases by the orthopedic industry since the 1970's. The option to stabilize an implant through ingrowth of bone or soft tissue provides a method to achieve long term fixation with biological material and eliminates complications associated with cement.

Figure 1A:
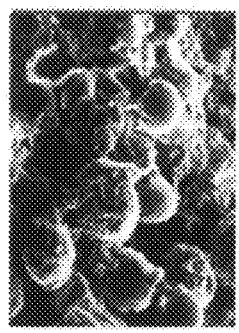
FIGS. 1A, 1B, 1C and 1D shows four photographs of different implant surfaces for bone growth attachment.
Figure 1B:
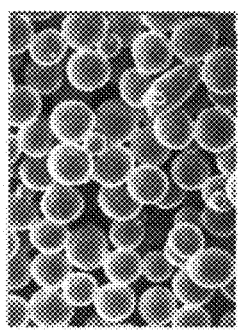
Figure 1C:
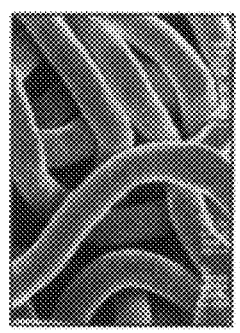
Figure 1D:
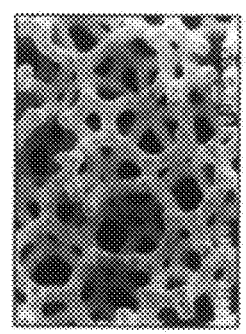

Current methods for implant fixation are through a porous surface created by layers of sintered beads, plasma sprayed surface, titanium wire and other micro and macro surfaces providing for a mechanical lock with bone. FIGS. 1A, 1B, 1C and 1D are photographs depicting different surfaces for bone growth attachment. FIG. 1A illustrates Scanning Electron Microscopy (SEM) image of the plasma sprayed porous surface. FIG. 1B illustrates an SEM image of sintered bead porous surface. FIG. 1C illustrates an image of a fiber porous surface and FIG. 1D illustrates an image of a porous tantalum structure with interconnected porosity. Most of these fixation surfaces are attached to a metal substrate (i.e. titanium, cobalt chrome), which has flexural modulus magnitudes well above that of bone. Titanium has a modulus of 100-110 GPa (14,503,774 to 15,954,151 psi) while bone has at best a modulus of 20.7 GPa, (3,002,281 psi), which is about 20 percent of the modulus of the implant. Cobalt-chromium alloy has an even higher modulus than titanium. When load is applied to the implant, the implant shields the bone from receiving stress, which causes bone resorption. The implant flexes very differently from the bone and therefore applies enormous pressures at the bone to when stress is applied to the bone requiring the bone to flex.

Figure 2:
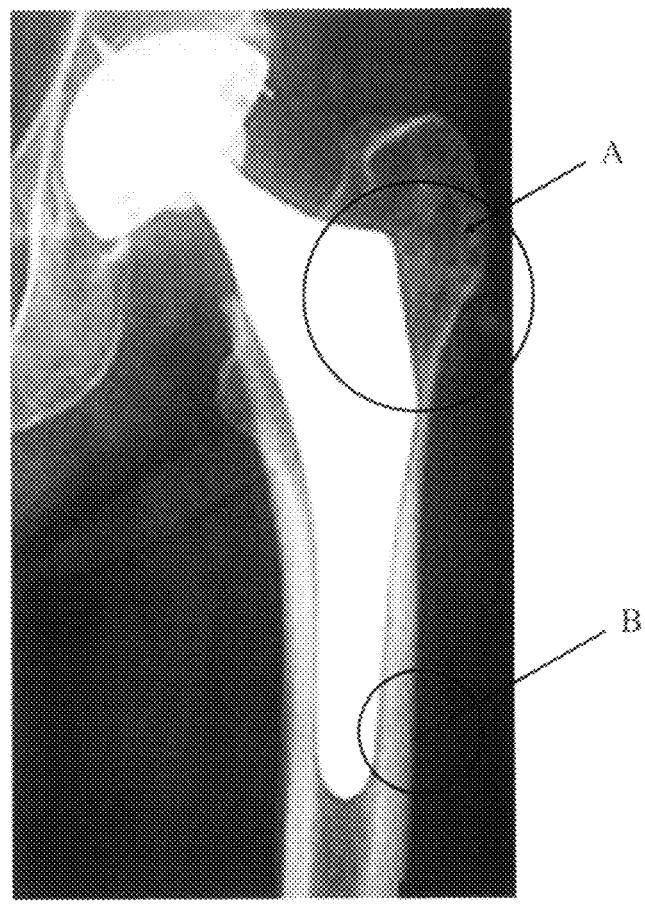
FIG. 2 illustrates an x-ray radiograph that illustrates bone resorption and distal end bone cortices thickening when a stiff prior art femoral hip stem is used.

Many clinical examples demonstrate adverse reactions of the bone due to an implant, which is too stiff. Under load, the deformation of the implant is much smaller than that of the bone due to the high elastic modulus of the implant. An implant with engineered flexural properties would allow the bone to be loaded more physiologically. Current implant technology provides implants, which are biocompatible but are much stiffer than the surrounding bone. In these cases the surrounding bone can be under stressed, sometimes causing bone resorption (body removes bone). The stiffness can generate very high local stresses at the distal tip of the implant because of its inflexibility. FIG. 2 illustrates an x-ray radiograph that clearly illustrates bone resorption when a stiff femoral hip stem is used especially over time due to stress shielding in the proximal bone and thickening of the distal cortices from over stressing at the stem tip. In this x-ray radiograph shown is of a conventional bone implant after one year of life. The implant has healed in this time period but the bone tissue has been resorbed in the proximal region A of a well-healed implant due to stress shielding. However, the portion B at the distal end of implant has bone thickening due to excessive flexural overstressing of the bone due to a stiff implant. This scenario of highly localized stresses can cause patient thigh pain and increased bone formation in an attempt to deal with the increased stress. The stem tip issue usually generates thigh pain during this remodeling and can still result in continued pain over one year following the original surgery. An implant, which provides more physiological load transfer to the bone establishes improved long term fixation, better density and quality of the surrounding bone and an implant reconstruction which is less painful. The high modulus of the implant stem prevents flexing of the implant and a very large load is applied to the bone at the distal end creating bone thickening. The thigh pain is caused by the bone thickening as well as loss of bone in the proximal region. Eventually, the loss of bone in the proximal region is so severe that a larger femoral cavity has to be reamed out to implant a larger femoral stem in the reamed cavity.

Figures 4A, 4B:
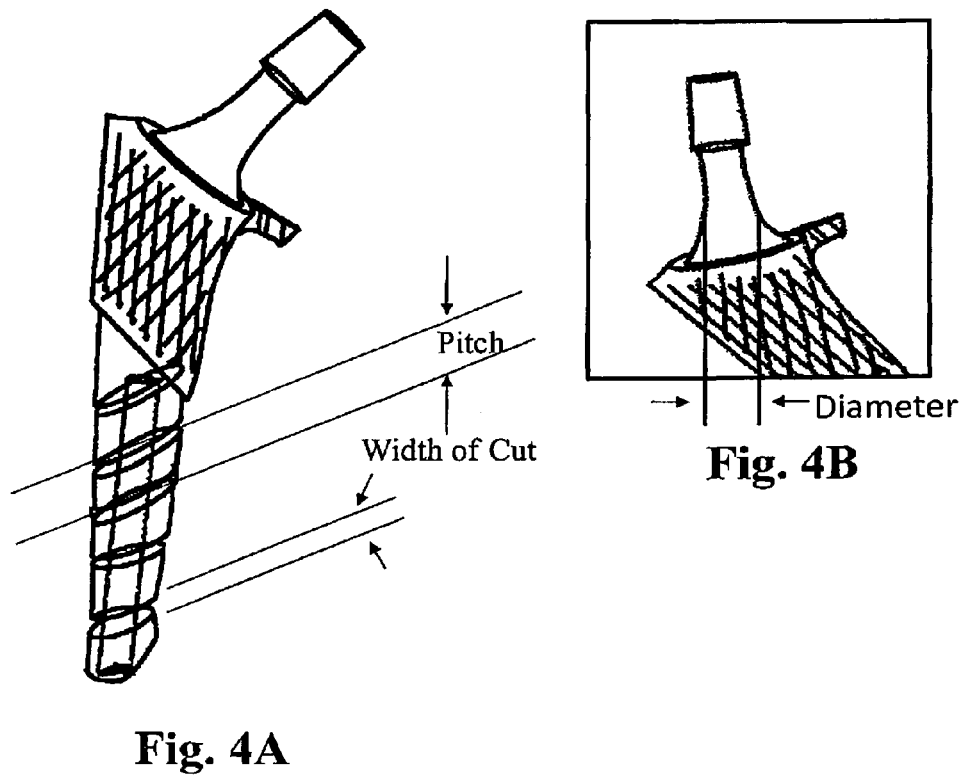
FIGS. 4A and 4B shows a top plan and top cross-sectional view, respectively, of the improved load bearing implant.

FIG. 3a illustrates an embodiment of the improved load bearing implant, shown generally at 10. FIGS. 3b-3d illustrate blow-up inclined and/or longitudinal cuts relative to the implant centerline in the proximal portion. FIGS. 4A and 4B (collectively, FIG. 4) illustrates top plan view and top cross-sectional views, respectively, of the improved load bearing implant to better illustrate the design. FIG. 4A shows the side view of the implant while FIG. 4B shows the top view of the implant. The implant 10 is preferably made from titanium. The design can utilize spiral cuts in the material (as shown) in the distal stem portion, longitudinal (FIG. 3c; longitudinal cuts shown at 13") or inclined (FIG. 3b; inclined cuts shown at 13') cuts relative to the implant centerline in the proximal portion, and or a combination of these cuts (FIGS. 3d; 13" and 13'). The proximal portion has a plurality of modulus decreasing features including longitudinal, inclined stress reducing cuts or slots, thereby increasing load transfer to the bone area in the proximal region. The objective of the invention is to allow the loaded implant to flex in a similar manner as the bone normally does. The flex cuts would be of sufficient width to prevent metal to metal contact when the implant is loaded. preventing metal to metal contact, the design avoids the problem of metal wear debris being generated from the implant as it is loaded.

The implant 10 has a similar geometry to other hip stems composed of a taper fitting 11, a neck-collar area 12, a proximal stem portion 13 and a distal stem portion 14 having flexural cuts 15 forming segments, herein spirals 16 along its length in the distal stem portion, providing flex to hollow distal stem 14. The neck-collar area 12 is of adequate length to provide appropriate stretch for soft tissue. Flexural cuts 15 are of a sufficient fixed selected width and depth to prevent adjacent surfaces of the segments, in this illustration spirals 16, from touching. Preferably, the flexural cuts 15 form a spiral configuration, as shown, yielding spiral segments along its length, providing flex to the hollow distal stem. Alternatively, the flexural cuts 15 are longitudinal cuts relative to the implant centerline, or horizontal cuts relative to the implant centerline, and/or a combination of spiral, longitudinal and/or horizontal cuts. The design of a more flexible femoral hip stem is accomplished through a hole 17 along the centerline of the stem 14 and with flexural cuts 15 forming spirals 16 along the stems length. Both the hole 17 diameter and the pitch between the spiral cuts 15 can be adjusted to create different flexural characteristics depending on the application. An important aspect of the flexural cuts is that they are of sufficient width for the application to prevent the adjacent surfaces from touching and potentially generating wear debris.

While the conventional femoral hip stem is a solid piece of metal and is very stiff relative to the stiffness of the bone (100× stiffer for cobalt chrome and 5 to 10× stiffer for titanium 6Al-4V), the Improved Load Bearing Implant herein is hollow. In order to bring the stem into better compliance with the bone, the stem portion is hollowed and has a spiral cut made along its length, as seen in FIG. 3, and FIG. 4. This provides the implant with an ability to flex in this area like a spring would. This added flexural property could be specifically designed to be in close proximity to the natural bone thereby allowing for a more physiological stress transfer and better bone remodeling.

The other benefits associated with the ability of the implant to flex are better fit to the internal canal geometry of the bone and reduction of stem tip stresses, as illustrated in FIG. 3. The former has resulted in creating left and right implants in many competitive systems in order for them to fit the internal canal. The latter creates post-operative thigh pain created by high stresses at the stem tip. The flex design of the stem can reduce or eliminate that problem.

Figure 5A:
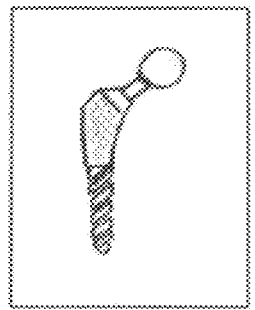
FIGS. 5A, 5B, 5C, 5D, 5E, 5F, 5G and 5H shows eight schematic illustrations depicting use of stress relief features in implants of other geometry
Figure 5B:
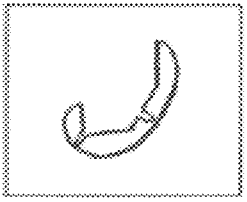
Figure 5C:
Figure 5D:
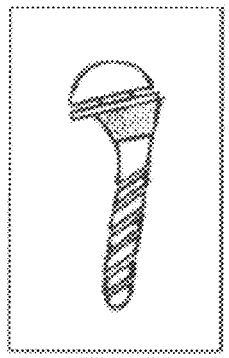
Figure 5E:
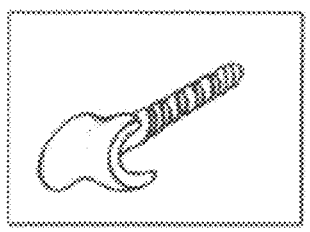
Figure 5F:
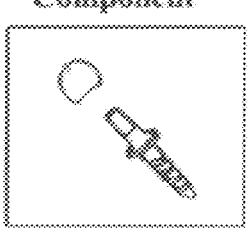
Figure 5G:
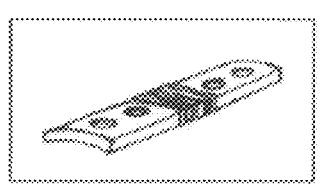
Figure 5H:
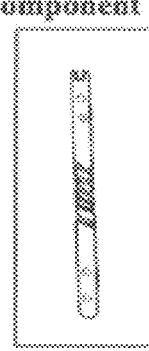

In addition to the femoral stem implant, this methodology of elimination of stress shielding as well as providing an implant modulus matching the bone modulus may be used in several geometries of bone implants. FIG. 5A, FIG. 5B, FIG. 5c, FIG. 5D, FIG. 5E, FIG. 5F, FIG. 5G and FIG. 5H depict use of stress relief features in implants of other geometry. FIG. 5A depicts in detail, the elements of the present invention. FIGS. 5B through 5H illustrate a number of examples of possible implants. Some of the examples do not have a central aperture, but sufficient cuts in various orientations are provided at appropriate width and depth, and spacing to provide desired flexural characteristics as well as preventing bone resorption. Examples 5B through 5H detail different variants for implants with one or more of longitudinal, spiral cuts facilitating flexure as detailed in the present invention. Examples include
  i. Hip stem for a total hip replacement (FIG. 5A);
  ii. Femoral Head replacement for the hip (FIG. 5B);
  iii. Knee femoral component (FIG. 5C);
  iv. Knee tibial component (FIG. 5D);
  v. Humeral Component for a shoulder replacement (FIG. 5E);
  vi. Elbow Replacement Humeral Component (FIG. 5F);
  vii. Bone plates (FIG. 5G); and
  viii. Interlocking nails (FIG. 5H)

Having thus described the invention in rather full detail, it will be understood that such detail need not be strictly adhered to, but that additional changes and modifications may suggest themselves to one skilled in the art, all falling within the scope of the invention as defined by the subjoined claims.

What is claimed is:

1. A load bearing implant for medical applications, comprising:
   a. a femoral implant stem having a male locking tapered fitting adapted for attachment to a internal female taper of a head that locks the head to a femoral implant stem;
   b. a neck-collar area providing an anatomical distance between a center of said head and a position of said femoral implant stem during implantation so as to provide appropriate stretch for soft tissue;
   c. said femoral implant stem being made from biocompatible metal having a proximal portion and a tapered distal portion;
   d. said proximal portion of femoral implant stem being solid and coated with a bone ingrowth coating having an attachment feature for firm attachment to bone within a bone cavity;
   e. said proximal portion having a plurality of modulus decreasing features including a combination of overlapping and intersecting longitudinal stress reducing cuts or slots and inclined cuts relative to a centerline of the implant thereby increasing load transfer to the bone area in the proximal region and preventing long term bone resorption, wherein the longitudinal stress reducing cuts or slots run parallel relative to the centerline of the implant and the inclined cuts run at an angle relative to the centerline;
   f. said tapered distal portion having a central aperture whereby the wall thickness in the distal portion decreases progressively towards a distal end, said central aperture terminating within said distal portion, wherein the central aperture extends from a bottom edge of the tapered distal portion and terminates at a top edge of the tapered distal portion so that said tapered distal portion forms a hollow distal stem;
   g. said tapered distal portion having a plurality of modulus decreasing features including lateral flexural cuts or slots on the outer surface forming a continuous helix along the entire length of the hollow tapered distal portion providing flexibility;
   h. said cuts or slots on the outer surface of said distal portion having a pre-selected uniform width and a uniform depth and being spaced apart at a distance from each other so that the slots allow flexing of the distal portion;

whereby the combination of cuts or slots in the distal portion and central cylindrical aperture allow progressive flexing of the distal end, thereby minimizing excessive loading of the bone tissue, and appropriate selection of slots, depth of slots and spacing between slots prevents metal to metal contact on the adjacent surfaces of the cuts or slots during flexure preventing generation of wear debris.

2. A load bearing implant for medical applications as recited by claim 1, wherein said bone ingrowth coating in the proximal portion of femoral implant stem is layers of sintered beads.

3. A load bearing implant for medical applications as recited by claim 1, wherein said bone ingrowth coating in the proximal portion of femoral implant stem is plasma sprayed surface of titanium beads.

4. A load bearing implant for medical applications as recited by claim 1, wherein said bone ingrowth coating in the proximal portion of femoral implant stem is sintered titanium wire.

5. A load bearing implant for medical applications as recited by claim 1, wherein said femoral implant stem is made from bio-compatible alloy.

6. A load bearing implant for medical applications as recited by claim 5, wherein said femoral implant stem is made from titanium alloy.

7. A load bearing implant for medical applications as recited by claim 5, wherein said femoral implant stem is made from cobalt chromium alloy.

8. A load bearing implant for medical applications as recited by claim 1, wherein said bone ingrowth coating has attachment features and said modulus decreasing features are employed for implants, wherein said implants are selected from the group consisting of femoral head replacement for the hip and a knee femoral component.

* * * * *